United States Patent
Wu et al.

[11] Patent Number: 5,410,077
[45] Date of Patent: Apr. 25, 1995

[54] CONTROLLED EPOXIDATION OF PROPYLENE

[75] Inventors: Chung-Nan T. Wu, Houston; Mark E. Taylor, Orange; Mark A. Mueller, Austin, all of Tex.

[73] Assignee: Texaco Chemical Company, White Plains, N.Y.

[21] Appl. No.: 148,226

[22] Filed: Nov. 8, 1993

[51] Int. Cl.$^6$ .................. C07D 301/19; C07D 303/04; C07C 27/16; C07C 31/12
[52] U.S. Cl. ................................. 549/529; 568/909.8
[58] Field of Search ......................................... 549/529

[56] References Cited

U.S. PATENT DOCUMENTS 3,666,777  5/1972  Sorgenti ............................ 549/529
5,216,182  6/1993  Marquis et al. .................... 549/529

*Primary Examiner*—Joseph E. Evans
*Attorney, Agent, or Firm*—James L. Bailey; Kenneth R. Priem; Carl G. Ries

[57] ABSTRACT

In a regulated process wherein propylene is reacted with tertiary butyl hydroperoxide in solution in tertiary butyl alcohol to produce propylene oxide and tertiary butyl alcohol in a reactor system comprising a first isothermal segment comprising a plurality of at least four sequentially interconnected internally cooled reactors, and a second adiabatic segment, an initial feed mixture is continuously charged to the first reactor, comprising propylene and a recycle stream composed of about 25 to about 75 wt. % of the combined weight of said propylene and said recycle stream, a plurality of feed streams comprising a tertiary butyl alcohol solution of tertiary butyl hydroperoxide and molybdenum catalyst are charged to each of at least four sequentially interconnected reactors, and about 60 to 80 wt % of the tertiary butyl hydroperoxide is converted in the isothermal segment; the recycle stream being removed at the end of the isothermal segment and the remainder of the intermediate reaction mixture being passed through the adiabatic segment where additional tertiary butyl hydroperoxide is converted.

20 Claims, 2 Drawing Sheets

ISOTHERMAL SEGMENT

CONTROLLED EPOXIDATION OF PROPYLENE

BACKGROUND OF THE INVENTION

1. Technical Field of the Invention

This invention relates to the regulated epoxidation of propylene. More particularly, this invention relates to a continuous process for the regulated reaction of propylene with tertiary butyl hydroperoxide in solution in tertiary butyl alcohol in the presence of an epoxidation catalyst to provide propylene oxide and additional tertiary butyl alcohol.

More particularly, this invention relates to a continuous flow controlled process for the preparation of propylene oxide and tertiary butyl alcohol by the continuous reaction of tertiary butyl hydroperoxide with propylene in solution in tertiary butyl alcohol in the presence of a soluble molybdenum catalyst, wherein the process is conducted in a plural stage reactor system comprising a first isothermal segment comprising a plurality of at least four serially connected internally cooled reactors (preferably 5 to 10 reactors) and a second adiabatic segment (preferably containing 4 to 10 serially interconnected reactors).

An initial feed mixture comprising propylene and a recycle stream is continuously charged to a first internally cooled reactor of the isothermal segment, the recycle stream comprising about 25 to about 75 wt. % of the combined weight of the propylene and the recycle stream (and more preferably comprising 40 to 60 wt. %). A plurality of tertiary butyl hydroperoxide feed streams are charged to each of at least four sequentially interconnected internally cooled reactors of the isothermal segment, said tertiary butyl hydroperoxide feed streams comprising a tertiary butyl alcohol solution of tertiary butyl hydroperoxide and molybdenum catalyst.

Reaction conditions of temperature, pressure, internal cooling and time are maintained in the isothermal segment sufficient to provide for a conversion of about 50 to 80 wt. % of the tertiary butyl hydroperoxide (and preferably about ½ to ⅔) to thereby provide an intermediate reaction product containing unreacted propylene and unreacted tertiary butyl hydroperoxide.

The said recycle stream is removed from the intermediate reaction product and recycled as aforesaid, the recycle stream being removed in an amount such that it constitutes from about 25 to about 75 wt. % (more preferably about 40 to 60 wt. %) of the initial feed mixture, and the remainder of the intermediate reaction product is charged to the adiabatic segment where the unreacted propylene and the unreacted tertiary butyl hydroperoxide are further reacted with each other under reaction conditions of temperature, pressure, and time sufficient to convert an additional 15 to 30 wt. % of the tertiary butyl hydroperoxide.

Still more particularly, this invention relates to a continuous flow-controlled process for the preparation of propylene oxide and tertiary butyl alcohol, as aforesaid, wherein the initial feed mixture is continuously flowed through an isothermal segment comprising a plurality of at least four serially connected internally cooled reactors, wherein a plurality of at least four tertiary butyl hydroperoxide feed streams is simultaneously charged to at least four sequentially interconnected internally cooled reactors to thereby provide the intermediate reaction product, wherein the said recycle stream is removed from the intermediate reaction product and recycled as described above, and wherein the remainder of the intermediate reaction product is charged to the adiabatic segment wherein an additional 15 to 30 wt. % of the tertiary butyl hydroperoxide is reacted with propylene to provide a final reaction product.

As an example, the isothermal segment may comprise about 10 serially connected internally cooled reactors and wherein six tertiary butyl hydroperoxide feed streams are charged to the first six of the serially interconnected internally cooled reactors. Also, the first of the tertiary butyl hydroperoxide feed streams preferably comprises about ½ to ⅔ of the total charge of tertiary butyl hydroperoxide to the isothermal segment.

The reaction conditions established in each of the isothermal and adiabatic segments may suitably include a temperature of about 100° to about 140° C. and more preferably about 110° to about 130° C. The pressure may suitably be in the range of about 200 to 700 psig and more preferably in the range of about 500 to 700 psig. The reaction time may suitably be from about 0.5 to 4 hours and, more preferably, from about 0.5 to 2 hours.

In practice, a desirable reaction temperature and pressure suitable to provide a desired reaction rate are predetermined and both the capacity and the cooling capacity of the internally cooled reactors are correlated with flow rate (i.e., reaction time) so that the predetermined temperature can be maintained throughout the isothermal and adiabatic segments.

2. Prior Art

The reaction of an olefin such as propylene with a hydroperoxide such as tertiary butyl hydroperoxide in solution in a solvent such as tertiary butyl alcohol in the presence of a soluble molybdenum catalyst is disclosed in Kollar U.S. Pat. No. 3,351,635. Kollar teaches that in general, from about 0.5 to 100 moles of olefin may be used per mole of hydroperoxide, the preferred molar ratio being within the range of about 2 to about 10 moles of olefin per mole of hydroperoxide.

Marquis et al. in U.S. Pat. No. 4,891,437 disclose an improvement on the Kollar process in the reaction of propylene with tertiary butyl hydroperoxide is concerned wherein the reaction is conducted in a medium composed of 60 wt. % or more of polar components which is formed by utilizing a molar ratio of propylene to tertiary butyl hydroperoxide of about 0.5 to 2 moles of charged propylene per mole of charged hydroperoxide, the reaction being conducted in solution in tertiary butyl alcohol in the presence of a molybdenum catalyst. Variations in the Marquis et al. process and in the preparation of catalysts useful therefore are disclosed in Marquis et al. U.S. Pat. No. 4,845,251 and U.S. Pat. No. 5,107,067.

British Patent No. 1,298,253 discloses a process for the staged reaction of propylene with tertiary butyl hydroperoxide in the presence of tertiary butyl alcohol and a soluble molybdenum catalyst wherein the reaction product from the first stage is fractionated to provide a lighter fraction which is recycled to the beginning of the first stage and a heavier fraction which is charged to the second stage of the epoxidation process.

Marquis et al. U.S. Pat. No. 4,992,566 and Marquis et al. U.S. Pat. No. 5,093,506 disclose single stage processes for the reaction of propylene with tertiary butyl hydroperoxide wherein the reaction product is fractionated to provide a propylene stream for recycle.

Russell U.S. Pat. No. 3,418,340 discloses a process for the production of propylene oxide by the reaction of propylene with tertiary butyl hydroperoxide involving a recycle of the propylene wherein the propylene is further fractionated to remove oxygen prior to recycle.

Stein et al. U.S. Pat. No. 3,849,451 discloses a process wherein propylene is reacted with tertiary butyl hydroperoxide in solution in tertiary butyl alcohol in a single stage compartmented reactor operated under conditions such that propylene and propylene oxide are vaporized during the course of the reaction and wherein the vapors are recovered and distilled to provide a propylene fraction for recycle.

D'Aubigne et al. U.S. Pat. No. 4,002,687 discloses a process for the hydroperoxidation of a hydrocarbon such as isopentane or isobutane with oxygen using a plurality of stages with water washing between stages.

BACKGROUND INFORMATION

Tertiary butyl hydroperoxide is a comparatively stable hydroperoxide. Nevertheless, it is a peroxide and subject to explosive autoxidation under improper conditions. The reaction of tertiary butyl hydroperoxide with propylene is a highly exothermic reaction, liberating about 60,000 calories of heat per gram mole of epoxide formed by the primary reaction. It is therefore of prime importance to maintain positive and accurate regulation of the reaction temperature during the epoxidation process in order to prevent a run away reaction.

It is known to achieve reaction control by conducting the reaction in a heat exchanger in indirect countercurrent contact with a heat exchange medium in order to remove excess heat of reaction as rapidly and efficiently as possible.

It is also known to moderate reaction temperature by conducting the reaction in the presence of a solvent.

Classically, both techniques have been utilized in the past in the preparation of propylene oxide from tertiary butyl hydroperoxide by conducting the reaction using a comparatively large quantity of solvent and also a large molar excess of propylene to tertiary butyl hydroperoxide, such as a molar ratio of more than 3 moles (e.g., 5 to 10 moles or more) of propylene per mole of tertiary butyl hydroperoxide. It is also known to conduct the reaction in a reactor provided with heat exchange control means, such as a jacket for the reactor or through the provision of internal immersed cooling coils or both.

Another problem that is encountered in the reaction of propylene with tertiary butyl hydroperoxide relates to selectivity. Although the primary reaction of the tertiary butyl hydroperoxide with propylene will result in the formation of propylene oxide and tertiary butyl alcohol, other oxygenated by-products can be and are formed in various amounts, including aldehydes, organic acids, esters, ketones, etc. Moreover, the propylene oxide that is formed can react with oxygenated by-products present in the reaction medium to further decrease the yield of propylene oxide.

Another problem as pointed out in Marquis et al. U.S. Pat. No. 4,891,437, is the tendency of propylene to react with itself under epoxidation conditions to form an addition product containing 6 or more carbon atoms. These hydrocarbon by-products are particularly pernicious in that they tend to codistill with and to be present in the final propylene oxide product where they significantly and adversely affect its quality. This problem can be minimized by use of a comparatively low mole ratio of propylene to tertiary butyl hydroperoxide, such as a molar ratio of about 1 to about 3 moles of propylene per mole of tertiary butyl hydroperoxide.

The use of low mole ratios of 1 to 3 moles of propylene per mole of tertiary butyl hydroperoxide creates other problems, however. Typically the tertiary butyl hydroperoxide is charged to the process as a tertiary butyl hydroperoxide feed stream comprising a tertiary butyl alcohol solution containing about 35 to about 60 wt. % of tertiary butyl hydroperoxide admixed with, correspondingly, about 65 to about 40 wt. % of tertiary butyl alcohol and about 0.1 to about 1 wt. % of a soluble catalyst comprising a complex of molybdenum with ethylene glycol. If the propylene and tertiary butyl hydroperoxide feed stream are charged in the indicated proportions, the advantage obtained in lowering the vapor pressure of the system to compensate for the volatility of propylene and propylene oxide is offset by the high concentration of tertiary butyl hydroperoxide which makes temperature difficult to control because of the rapid build up of heat in the reactors brought about by the high concentration of tertiary butyl hydroperoxide.

SUMMARY OF THE INVENTION

In accordance with the present invention, the foregoing and other problems are ameliorated through the provision of a process wherein the continuous regulated reaction of propylene with tertiary butyl hydroperoxide in solution in tertiary butyl alcohol in the presence of a soluble molybdenum catalyst is conducted in a plural stage reactor system comprising a first isothermal segment comprising a plurality of at least four serially connected internally cooled reactors (preferably 5 to 10 reactors) and a second adiabatic segment (preferably containing 4 to 10 serially interconnected reactors).

In accordance with the process of the present invention, an initial feed mixture comprising propylene and a recycle stream is continuously charged to the first internally cooled reactor, the recycle stream comprising about 25 to about 75 wt. %, of the combined weight of said propylene and said recycle stream, (and more preferably comprises 40 to 60 wt. %), and a plurality of tertiary butyl hydroperoxide feed streams are charged to each of at least four sequentially interconnected internally cooled reactors, said tertiary butyl hydroperoxide feed streams comprising a tertiary butyl alcohol solution of tertiary butyl hydroperoxide and molybdenum catalyst.

Reaction conditions of temperature, pressure, internal cooling and time are maintained in the isothermal segment sufficient to provide for a conversion of about 50 to 80 wt. % of the tertiary butyl hydroperoxide (and preferably about ½ to ⅔) to thereby provide an intermediate reaction product containing unreacted propylene and unreacted tertiary butyl hydroperoxide, from which the said recycle stream is removed. The remainder of the intermediate reaction product is charged to the adiabatic segment where the unreacted propylene and the unreacted tertiary butyl hydroperoxide are further reacted with each other under reaction conditions of temperature, pressure, and time sufficient to convert an additional 15 to 30 wt. % of the tertiary butyl hydroperoxide and to provide a final reaction product.

The final reaction product will typically comprise unreacted propylene, propylene oxide, tertiary butyl alcohol, unreacted tertiary butyl hydroperoxide, oxygen-containing by-product impurities and molybdenum catalyst residue. The propylene and propylene oxide, because of their comparatively high volatility can be removed from the final reaction mixture by distillation.

In accordance with a preferred embodiment of the present invention, the process is carried out continuously in a reactor system, as previously described, the system comprising a first isothermal reactor segment containing about 10 serially connected internally cooled reactors and in a second adiabatic segment containing about 6 externally cooled reactors wherein:

Six tertiary butyl hydroperoxide feed streams are sequentially charged to each of the first six sequentially interconnected internally cooled reactors of the isothermal segment, about ½ to ⅔ of the total amount of tertiary butyl hydroperoxide charge being charged to the first of said internally cooled reactors and the remainder of the tertiary butyl hydroperoxide being charged in equal amounts to the remaining four of the five sequentially interconnected internally cooled reactors.

The epoxidation reaction conditions utilized in the isothermal epoxidation segment may suitably include a temperature of about 50° to about 180° C. and a reaction time of about 0.3 to about 3 hours. More preferably, the reaction will be conducted at a pressure of about 400 to about 800 psig, a reaction temperature of about 80° to about 140° C. and a reaction time of about 0.5 to about 2 hours.

Reaction conditions are preferably adjusted in the isothermal segment to provide for about a 60 to about a 80% conversion of the tertiary butyl hydroperoxide and for the recycle of a recycle stream comprising about 25 to about 75 wt. % of the combined weight of the propylene charge stream and the tertiary butyl alcohol solution.

Preferably reaction conditions should be maintained such that all of the reactors in the isothermal segment have about the same inlet temperature and such that about 60 to 80 wt. % of the tertiary butyl hydroperoxide is reacted with the propylene in the isothermal segment. This is accomplished in accordance with the present invention by allocating the amount of tertiary butyl hydroperoxide in the tertiary butyl hydroperoxide charge streams for the reactor under consideration such that the amount of heat liberated by the reaction of propylene with tertiary butyl hydroperoxide in the selected reactor will be an amount that can be removed from the mixture by internal cooling.

A problem involved in the recycle of reactor effluent from the isothermal segment arises in that the recycle stream is at a temperature of 100° to 140° C. and contains tertiary butyl hydroperoxide and possibly other hydroperoxide reaction products which may be less thermally stable than the tertiary butyl hydroperoxide. Therefore, when a pump is utilized to provide the motive force for recycling the recycle stream, care must be taken to avoid a potential source of ignition, such as a spark generated by the equipment. Failure of a mechanical pump can also lead to a runaway reaction. A mechanical pump may provide an ignition source in the event of the failure of a bearing, a rotor or some other part which permits the creation of a local hot spot. Also, it is not uncommon for a mechanical pump to experience deterioration of the seals which can lead to the release of environmentally noxious or hazardous materials.

In accordance with a modified form of the present invention, these and other problems are ameliorated through the provision of a jet pump or eductor in order to provide the motive force for transporting the recycle stream from the effluent end of the isothermal segment to the front end.

DESCRIPTION OF THE PREFERRED EMBODIMENT

Figure 1:
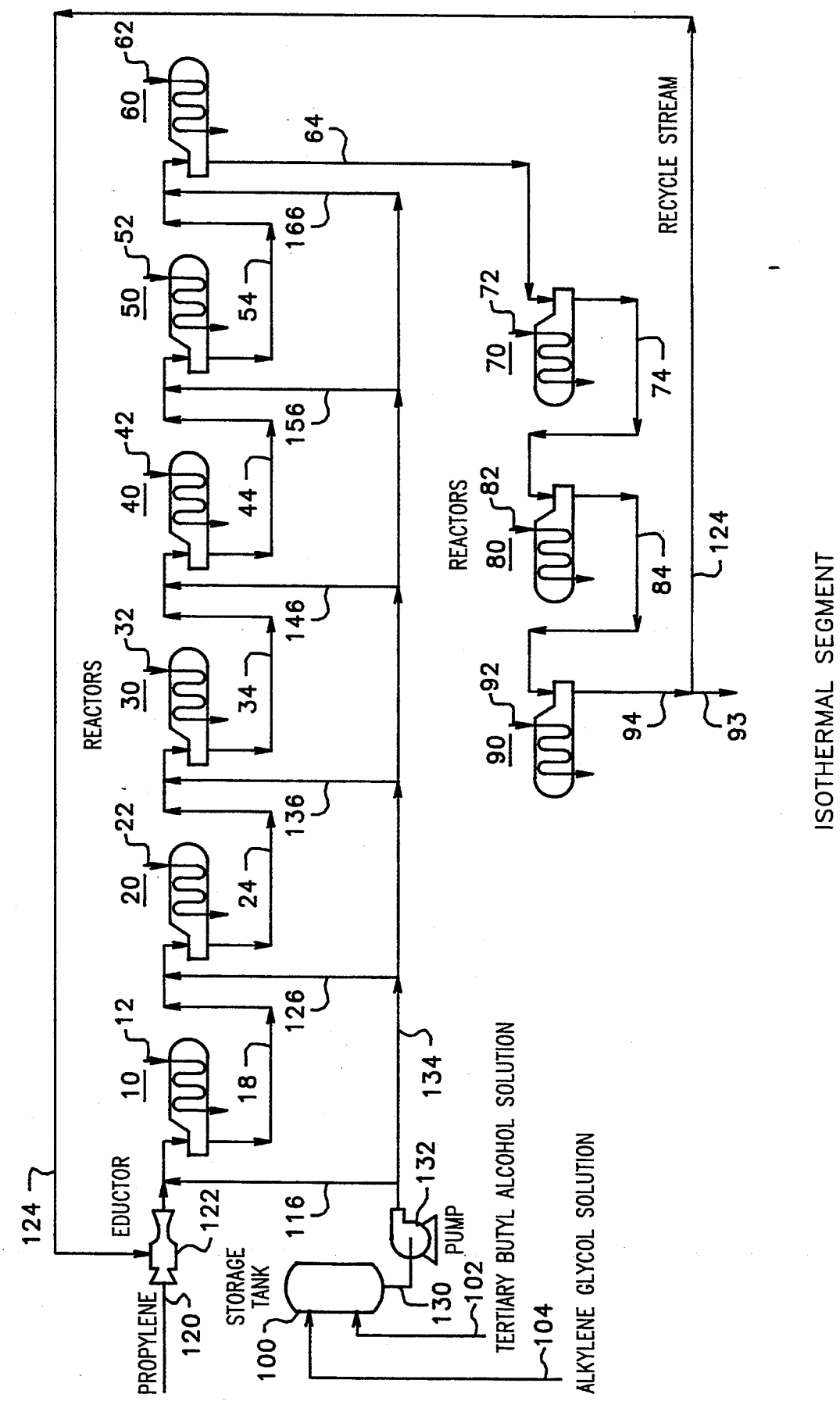
FIG. 1 is a schematic flow sheet illustrating a preferred configuration of the isothermal segment used in a preferred practice of the present invention.

Turning now to the drawings, there are shown schematic flow sheets illustrating a preferred method of practicing the process of the present invention. In the drawings, conventional parts, such as valves, pumps, temperature sensors, pressure sensors, heaters, coolers, flow control regulation apparatus, etc., have been omitted.

In accordance with the present invention, as illustrated by FIG. 1, there is provided a reactor system comprising an isothermal segment which comprises a plurality of at least four, and more preferably from about 5 to 10, sequentially interconnected internally cooled reactors, such as a sequence of 9 reactors illustrated in FIG. 1 and designated by the numbers 10, 20, 30, 40, 50, 60, 70, 80 and 90. Internal cooling can be accomplished in any suitable manner; for example, through the provision of internal cooling coils in each reactor and designated, respectively, by the numbers 12, 22, 32, 42, 52, 62, 72, 82 and 92.

Suitable means, such as a holding tank 100 is provided for the storage of a tertiary butyl hydroperoxide feed. The storage tank is suitably maintained at an ambient temperature or lower to provide for safe storage of the tertiary butyl hydroperoxide. The tertiary butyl hydroperoxide feed will suitably comprise a tertiary butyl alcohol solution containing about 35 to about 60 wt. % of tertiary butyl hydroperoxide admixed with, correspondingly, about 65 to about 40 wt. % of tertiary butyl alcohol and about 0.1 to about 1 wt. % of a soluble catalyst comprising a suitable molybdenum catalyst such as a an alkylene glycol solution of a complex of molybdenum with the alkylene glycol, such as an ethylene glycol solution of a complex of molybdenum with ethylene glycol, of the type disclosed and described in Marquis et al. U.S. Pat. No. 4,626,596 dated Dec. 2, 1986. The tertiary butyl alcohol solution of tertiary butyl hydroperoxide is charged to the holding tank from a suitable source (not shown) by a line 102 and the alkylene glycol solution is charged to holding tank 100 from a suitable source (not shown) by a line 104.

In order to initiate the process of the present invention, propylene is continuously charged from a suitable source (not shown) by a line 120 to an eductor 122 leading by line 123 to the first of the internally cooled reactors 10. A recycle stream 124, obtained in a manner to be described, is continuously educted into the propylene charge stream 120, the recycle stream comprising about 25 to about 75 wt. % of the combined weight of the propylene charge stream and the recycle stream, and more preferably, from about 40 to 60 wt. % of the combined weight. A tertiary butyl hydroperoxide feed stream is continuously discharged from holding tank 100 by a discharge line 130 leading to a pump 132 from which it is discharged by a feed line 134.

A predetermined portion of the tertiary butyl hydroperoxide feed stream is charged by a branch line 116 to the eductor discharge line 123 and thence, together with the propylene and the recycle stream, to the first internally cooled reactor 10. The effluent from the reactor 10 is fed by a transfer line 18 to the second reactor 20, from thence by a transfer line 24 to the third reactor 30, from thence by a transfer line 34 to the fourth reactor 40, from thence by a transfer line 44 to the fifth reactor 50, from thence by a transfer line 54 to the sixth reactor 60, from thence by a transfer line 64 to the seventh reactor 70, from thence by a transfer line 74 to the eighth reactor 80, and from thence by a transfer line 84 to the ninth reactor 90.

Suitably, from about 50 to 80 wt. % of the tertiary butyl hydroperoxide feed stream discharged from the pump 32 is fed to the eductor discharge line 123 by the branch line 116 and, more preferably, from about ½ to about ⅔ of the tertiary butyl hydroperoxide feed stream discharged from the pump 32 is fed to the eductor discharge line 123 by the branch line 126 The remainder of the tertiary butyl hydroperoxide feed stream discharged from the pump 32 is fed in equal aliquot portions to a desired predetermined number of immediately sequential reactors, such as from 3 to 6 reactors. Thus, in the illustrated embodiment, the remainder of tertiary butyl hydroperoxide feed stream discharged from the pump 32 is fed in five equal aliquot portions through branch lines 126, 136, 146, 156 and 166 to, respectively, the second reactor 20, the third reactor 30, the fourth reactor 40, the fifth reactor 50 and the sixth reactor 60.

Within the reactors comprising the isothermal segment reaction conditions of time, temperature, and pressure are established so as to convert from about 60 to about 80 wt. % of the charged tertiary butyl hydroperoxide. The reaction conditions to be utilized in the isothermal segment may include a pressure sufficient to maintain the reactants in liquid phase, such as a pressure of about 500 to about 700 psig, a reaction temperature of about 50° to about 180° C., such as a temperature of about 100° to about 130° C., and a reaction time of about 0.3 to about 3 hours, and more preferably from about 0.5 to about 2 hours. The reactor effluent from the last of the isothermal reactors 90 is discharged by a line 94 which is provided with a branch line 124 from which the recycle stream is removed and with a second line 93 leading to the adiabatic reaction segment 2 where an additional 15 to 30 wt. % of the tertiary butyl hydroperoxide is converted.

Figure 2:
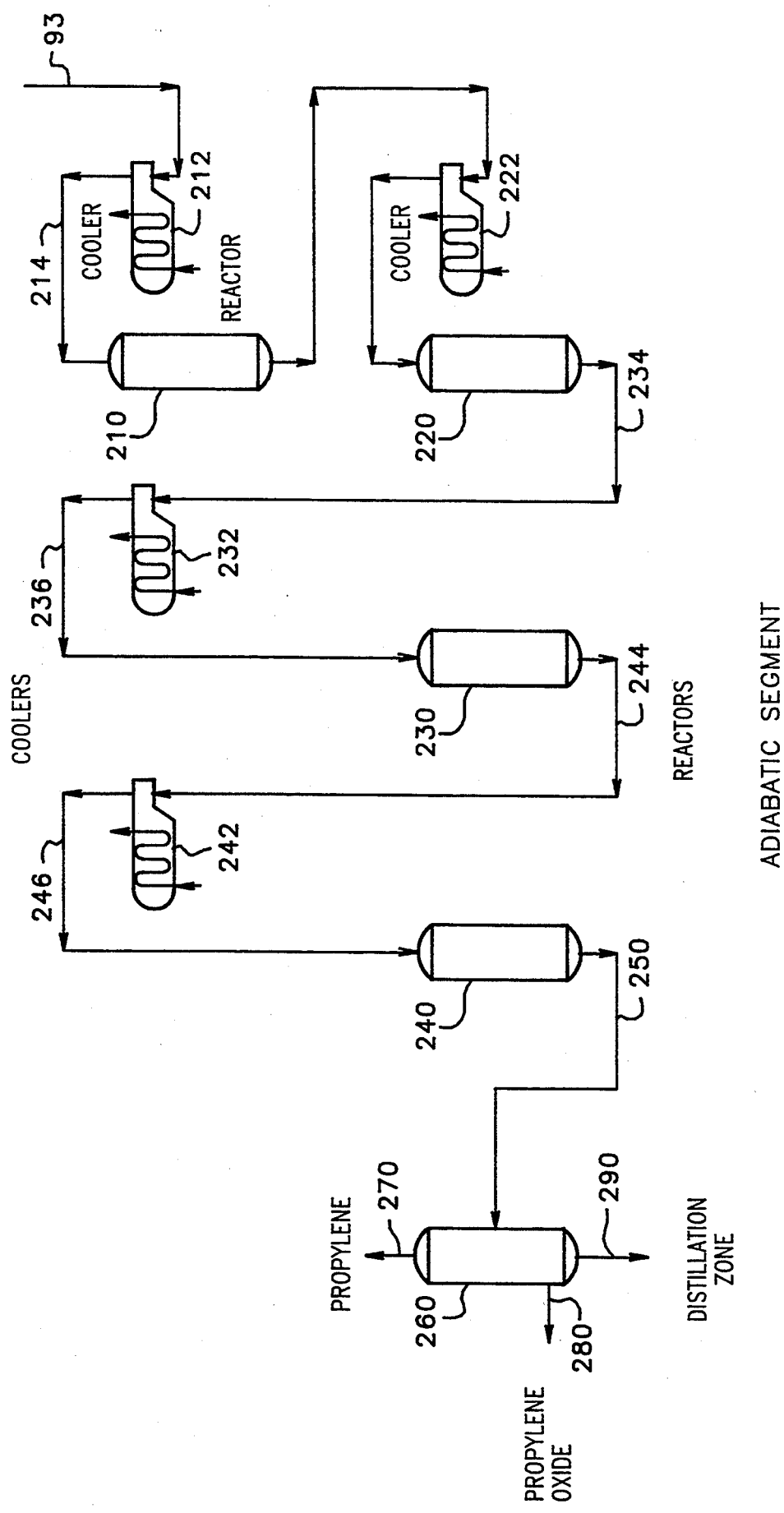
FIG. 2 is a schematic flow sheet illustrating a preferred configuration of the adiabatic segment used in the practice of the present invention.

Turning now to FIG. 2, there is shown an adiabatic segment, which comprises a plurality of at least four, and more preferably from about 5 to 10 sequentially interconnected internally cooled reactors, such as a sequence of 4 reactors illustrated in FIG. 2 and designated by the numbers 210, 220, 230, and 240. External cooling can be accomplished in any suitable manner; for example, through the provision of external heat exchangers for each reactor and designated, respectively, by the numbers 212, 222, 232 and 242.

The unrecycled portion of the effluent 92 from the reactor 90 of the isothermal segment (FIG. 1) is charged by line 93 to a first external heat exchanger 212 where a desired temperature is established. From thence, the effluent is charged by a transfer line 214 to reactor 210. The effluent from the reactor 210 is fed by a transfer line 218 to the second external heat exchanger 222, from thence by a transfer line 224 to the second reactor 220, from thence by a transfer line 234 to the third external heat exchanger 232, from thence by a transfer line 236 to third reactor 230, from thence by a transfer line 244 to fourth external heat exchanger 242 and from thence by transfer line 246 to the fourth reactor 240.

The effluent from the fourth reactor 240, the final reaction product 250, is charged by a line 250 to a distillation zone comprising one or more distillation columns, such as a distillation column 260 where the final reaction product is separated into suitable fractions such as, for example, a propylene fraction 270 and a propylene oxide fraction 280. The remainder of the final reaction product is discharged by a line 290 for further processing in any suitable manner (not shown).

EXAMPLE

By way of example, about 3,500 parts per hour of propylene may be charged to the eductor 122 by the line 120 at a pressure of about 2300 psia and a temperature of about 135° C. and intimately mixed in the eductor 122 with about 7,000 parts per hour of a recycle stream 124. The recycle stream may comprise, for example, about 1,300 parts of propylene, about 1,200 parts of propylene oxide, about 3,700 parts of tertiary butyl alcohol and about 800 parts of tertiary butyl hydroperoxide. The stream 123 discharged from the eductor 122 is charged to the reactor 10.

The holding tank 100 may be filled with a solution of about 55 wt. % of tertiary butyl hydroperoxide in tertiary butyl alcohol by line 102 and a catalyst comprising an ethylene glycol solution of an ethylene glycol/molybdenum catalyst may be charged to holding tank 100 by the line 104. The holding tank 100 is held at an ambient temperature and pressure for safe storage and pumping of the solution. About 8,000 parts per hour of the solution of tertiary butyl hydroperoxide in tertiary butyl alcohol is discharged from the holding tank 100 by a line 130 leading to pump 132 where the solution is pressured to about 730 psia and discharged by line 134.

About 2,500 parts per hour of the tertiary butyl hydroperoxide stream 134 is routed by branch line 116 to the line 123 where it is mixed with the eductor discharge stream charged to the reactor 10.

Reaction conditions are established in the reactor 10, including a temperature of about 135° C. and a pressure of about 715 psia. Heat is internally removed from the reactor 10 by indirect contact with water in the cooling coil 12 located therein.

The first reaction product from the reactor 10 is discharged by a line 18 to which an additional 600 parts per hour of the tertiary butyl hydroperoxide is added by the branch line 126 leading from line 134. Thus augmented stream 18 is charged to the second reactor 20 where substantially the same reaction conditions of time, temperature and pressure are maintained; heat of reaction being removed by cooling water circulated through the reactor 20 by the cooling coil 22. In like manner, reactors 30, 40 50 and 60 are charged with the reaction mixture from the preceding reactor augmented, in each instance with about 600 parts per hour of the solution of tertiary butyl hydroperoxide in tertiary butyl alcohol. As the reaction solution flows through reactors 10–60, in the described fashion, the tertiary butyl hydroperoxide reacts with the propylene to form propylene oxide and additional tertiary butyl alcohol, thus progressively diluting the unreacted propylene and unreacted tertiary butyl hydroperoxide.

The reaction of the propylene and unreacted tertiary butyl hydroperoxide is continued by passing the reaction mixture from reactor 60 by line 62 to reactor 70, thence by line 72 to reactor 80 and thence by line 82 to reactor 90. Again, essentially the same reaction conditions of time, temperature and pressure are maintained in each of the reactors 70, 80 and 90 and heat is internally removed from the reactors by cooling water circulated therethrough by cooling coils 72, 82 and 92, respectively.

About 14,000 pounds per hour of reaction mixture is discharged from reactor 90 by line 92. Of this, about 7,000 pounds per hour is recycled to the eductor 122 by recycle line 124 and remaining 7,000 parts per hour is charged by line 93 to an adiabatic reaction segment comprising externally cooled reactors 210, 220, 230 and 240. Thus, the reaction mixture is charged by line 93 to external heat exchanger 212 where the reaction mixture is cooled to a temperature of about 125° C. at a pressure of about 545 psia by cooling water passed therethrough by line 212. From heat exchanger 212 the reaction mixture is charged by line 214 to adiabatic reactor 210 where a pressure of about 545 psia and a temperature of about 140° C. are maintained.

In like manner, the reaction mixture is sequentially passed through heat exchanger 222 to reactor 220, thence by line 234 to heat exchanger 232, thence by line 236 to reactor 230, thence by line 244 to heat exchanger 242, and thence by line 246 to reactor 240; essentially the same reaction conditions being maintained in all of the reactors 210-240.

The reaction product is discharged from reactor 240 by line 260 to a distillation zone 260 where it is separated into suitable fractions, such as a propylene fraction 270, a propylene oxide fraction 280 and heavier fractions such as fraction 290.

Having thus described our invention, what is claimed is:

1. In a regulated continuous process for preparing propylene oxide and tertiary butyl alcohol by reacting propylene with tertiary butyl hydroperoxide in solution in tertiary butyl alcohol in the presence of a soluble molybdenum catalyst, the improvement which comprises:

continuously conducting said process in a reactor system comprising a first isothermal segment comprising a plurality of at least four sequentially interconnected internally cooled reactors and a second adiabatic segment, continuously charging to the first of said internally cooled reactors of said isothermal segment an initial feed mixture comprising propylene and a recycle stream, said recycle stream comprising about 25 to about 75 wt. %, of the combined weight of said propylene and said recycle stream, separately continuously simultaneously charging a plurality of tertiary butyl hydroperoxide feed streams to each of at least four sequentially interconnected internally cooled reactors, said plurality of tertiary butyl hydroperoxide feed streams being charged at a rate such that a total of about 1 to about 3 moles of propylene is charged to said isothermal segment per mole of tertiary butyl hydroperoxide charged to said isothermal segment, said tertiary butyl hydroperoxide feed streams comprising a tertiary butyl alcohol solution of tertiary butyl hydroperoxide and molybdenum catalyst, adjusting the rate of tertiary butyl hydroperoxide charge and the rate of heat removal for each of said internally cooled reactors so as to maintain about the same inlet temperature for each of said internally cooled reactors and reacting a total of from about 50 to 80 wt. % of the charged tertiary butyl hydroperoxide with the charged propylene to form an intermediate reaction product, continuously removing a recycle stream from said intermediate reaction product and continuously recycling it to said isothermal segment as said recycle stream, continuously passing the remainder of the intermediate reaction product through the adiabatic segment and converting an additional 15 to 30 wt. % of the tertiary butyl hydroperoxide therein to thereby provide a final reaction product, and continuously recovering propylene oxide from said final reaction product.

2. A continuous process as in claim 1 wherein the isothermal segment comprises about 4 to 10 serially interconnected internally cooled reactors, wherein the adiabatic segment comprises about 4 to 10 serially interconnected reactors and wherein the said recycle stream is removed from the reaction product flowing from the last of the internally cooled reactors of the isothermal segment.

3. A continuous process as in claim 2 wherein at least five tertiary butyl hydroperoxide feed streams are sequentially charged to each of at least five sequentially interconnected internally cooled reactors, wherein about ⅓ to ⅔ of the total amount of charged tertiary butyl hydroperoxide is charged to the first of said internally cooled reactors and the remainder of the charged tertiary butyl hydroperoxide is charged in equal amounts to the remaining four of the five sequentially interconnected internally cooled reactors.

4. A continuous process as in claim 3 wherein the epoxidation reaction conditions include a temperature of about 100° to about 140° C., a pressure of about 200 to about 700 psig and a reaction time of about 0.5 to about 4 hours in both the isothermal segment and the adiabatic segment.

5. A continuous process as in claim 4 wherein the epoxidation reaction conditions include a temperature of about 110° to about 130° C., a pressure of about 500 to about 700 psig and a reaction time of about 0.5 to about 2 hours in both the isothermal segment and the adiabatic segment.

6. A continuous process as in claim 5 wherein the reaction conditions are adjusted in the isothermal segment to provide for about a 65 to about a 75% conversion of the tertiary butyl hydroperoxide and wherein the recycle stream comprises about 40 to 60 wt. % of the combined weight of the charged propylene and the recycle stream.

7. A continuous process as in claim 6 wherein the reaction conditions are adjusted in the isothermal segment to provide for about a 60 wt. % conversion of the charged tertiary butyl hydroperoxide in the isothermal segment.

8. In a regulated continuous process for preparing propylene oxide and tertiary butyl alcohol by reacting propylene with tertiary butyl hydroperoxide in solution in tertiary butyl alcohol in the presence of a soluble molybdenum catalyst, the improvement which comprises:

continuously conducting said process in a reactor system comprising a first isothermal segment comprising a plurality of at least six sequentially interconnected internally cooled reactors and a second adiabatic segment, preparing a tertiary butyl hydroperoxide feed stream comprising a tertiary butyl alcohol solution containing about 35 to about 60 wt. % of tertiary butyl hydroperoxide admixed with, correspondingly, about 65 to about 40 wt. % of tertiary butyl alcohol and about 0.1 to about 1 wt. % of a soluble molybdenum catalyst, continuously charging a plurality of tertiary butyl hydroperoxide feed streams to each of at least four sequentially interconnected internally cooled reactors, said plurality of tertiary butyl hydroperoxide feed streams being charged at a rate such that a total of about 1.1 to about 2.5 moles of propylene is charged to said isothermal segment per mole of tertiary butyl hydroperoxide charged to said isothermal segment, continuously mixing the first of said tertiary butyl hydroperoxide feed streams with a recycle stream and with propylene to form an initial charge mixture, and continuously introducing said initial charge mixture to the first of said internally cooled reactors, said recycle stream being about 25 to about 75 wt. %, of the combined weight of said propylene and said recycle stream, adjusting the rate of propylene charge and the rate of heat removal for each of said internally cooled reactors so as to maintain about the same inlet temperature for each of said internally cooled reactors and reacting a total of from about ⅔ to about ¾ of the charged tertiary butyl hydroperoxide with the propylene to form an intermediate reaction product, continuously removing a recycle stream from the intermediate reaction product and continuously recycling it to the first isothermal segment as said recycle stream, continuously passing the remainder of the intermediate reaction product through the adiabatic segment and converting an additional 15 to 30 wt. % of the tertiary butyl hydroperoxide therein to thereby provide a final reaction product comprising unreacted propylene, unreacted tertiary butyl hydroperoxide, tertiary butyl alcohol, dissolved molybdenum catalyst and oxygen-containing impurities, and continuously charging said final epoxidation product to a distillation zone and resolving it therein into distillation fractions including a distillate propylene fraction, and a distillate propylene oxide fraction.

9. A continuous process as in claim 8 wherein the isothermal segment comprises about 6 to 10 serially interconnected internally cooled reactors, wherein the adiabatic segment comprises about 5 to 10 serially interconnected reactors and wherein the said recycle stream is removed from the reaction mixture flowing from the last of the internally cooled reactors of the isothermal segment.

10. A continuous method as in claim 9 wherein at least six tertiary butyl hydroperoxide feed streams are sequentially charged to each of at least six sequentially interconnected internally cooled reactors, wherein about ½ to ⅔ of the total amount of tertiary butyl hydroperoxide is charged to the first of said internally cooled reactors and the remainder of the tertiary butyl hydroperoxide is charged in equal amounts to the remaining five of the six sequentially interconnected internally cooled reactors.

11. A continuous process as in claim 10 wherein the epoxidation reaction conditions include a temperature of about 100° to about 140° C., a pressure of about 200 to about 700 psig and a reaction time of about 0.5 to about 4 hours in both the isothermal segment and the adiabatic segment.

12. A continuous process as in claim 11 wherein the epoxidation reaction conditions include a temperature of about 110° to about 130° C., a pressure of about 500 about 700 psig and a reaction time of about 0.5 to about 2 hours in both the isothermal segment and the adiabatic segment.

13. A continuous process as in claim 12 wherein the reaction conditions are adjusted in the isothermal segment to provide for about a 65 to about a 75% conversion of the tertiary butyl hydroperoxide and wherein the recycle stream comprises about 40 to 60 wt. % of the combined weight of the charged propylene and recycle stream.

14. A continuous process as in claim 13 wherein the reaction conditions are adjusted in the isothermal segment to provide for about a 60 wt. % conversion of the charged tertiary butyl hydroperoxide.

15. In a regulated continuous process for preparing propylene oxide and tertiary butyl alcohol by reacting propylene with tertiary butyl hydroperoxide in solution in tertiary butyl alcohol in the presence of a soluble molybdenum catalyst, the improvement which comprises:

continuously conducting said process in a reactor system comprising a first isothermal segment comprising a plurality of at least six sequentially interconnected internally cooled reactors and a second adiabatic segment, preparing a tertiary butyl hydroperoxide feed stream comprising a tertiary butyl alcohol solution containing about 35 to about 60 wt. % of tertiary butyl hydroperoxide admixed with, correspondingly, about 65 to about 40 wt. % of tertiary butyl alcohol and about 0.1 to about 1 wt. % of a soluble catalyst comprising a complex of molybdenum with ethylene glycol, continuously charging a plurality of tertiary butyl hydroperoxide feed streams to each of at least six sequentially interconnected internally cooled reactors, said plurality of tertiary butyl hydroperoxide feed streams being charged at a rate such that a total of about 1.1 to about 1.5 moles of propylene is charged to the isothermal segment per mole of tertiary butyl hydroperoxide charged to said isothermal segment, continuously mixing the first of said tertiary butyl hydroperoxide feed streams with a recycle stream and with a propylene stream to form an initial charge mixture, and continuously introducing said initial charge mixture into the first of said internally cooled reactors, said recycle stream comprising about 25 to about 75 wt. % of the weight of said recycle stream and said propylene stream, establishing epoxidation reaction conditions in said isothermal segment and said adiabatic segment including a pressure of about 200 to 500 psig, a temperature of about 100° to about 130° C., and a reaction time for each segment of about 2 to about 4 hours, adjusting the rate of propylene charge and the rate of heat removal for each of said internally cooled reactors so as to maintain about the same inlet temperature for each of said internally cooled reactors and reacting a total of from about 60 to 80 wt. % of the charged tertiary butyl hydroperoxide with the charged propylene to form an intermediate reaction product, continuously removing a recycle stream from the intermediate reaction product and continuously recycling it to the first isothermal segment as said recycle stream, continuously passing the remainder of the intermediate reaction product through the adiabatic segment and converting an additional 15 to 20 wt. % of the tertiary butyl hydroperoxide therein, to thereby provide a final reaction product comprising unreacted propylene, unreacted tertiary butyl hydroperoxide, tertiary butyl alcohol, dissolved molybdenum/ethylene glycol catalyst and oxygen-containing impurities, and continuously charging said final epoxidation product to a distillation zone and resolving it therein into distillation fractions including a distillate propylene fraction, and a distillate propylene oxide fraction.

16. A continuous process as in claim 15 wherein the isothermal segment comprises about 5 to 10 serially interconnected internally cooled reactors, wherein the adiabatic segment comprises about 5 to 10 serially interconnected reactors and wherein the said recycle stream is removed from the reaction product flowing from the last of the internally cooled reactors of the isothermal segment.

17. A continuous process as in claim 16 wherein at least five tertiary butyl hydroperoxide feed streams are sequentially charged to each of at least five sequentially interconnected internally cooled reactors, wherein about $\frac{1}{3}$ to $\frac{2}{3}$ of the total amount of tertiary butyl hydroperoxide charge is charged to the first of said internally cooled reactors and the remainder of the tertiary butyl hydroperoxide is charged in equal amounts to the remaining four of the five sequentially interconnected internally cooled reactors.

18. A continuous process as in claim 17 wherein the epoxidation reaction conditions include a temperature of about 110° to about 140° C., a pressure of about 500 to about 700 psig and a reaction time of about 0.5 to about 2 hours in both the isothermal segment and the adiabatic segment.

19. A continuous process as in claim 18 wherein the reaction conditions are adjusted in the isothermal segment to provide for about a 65 to about a 75% conversion of the tertiary butyl hydroperoxide and wherein the recycle stream comprises about 40 to 60 wt. % of the combined weight of the charged propylene and the recycle stream.

20. A continuous process as in claim 19 wherein the reaction conditions are adjusted in the isothermal segment to provide for about a 60 wt. % conversion of the charged tertiary butyl hydroperoxide.

* * * * *